United States Patent [19]

Mirviss

[11] Patent Number: 5,001,249

[45] Date of Patent: Mar. 19, 1991

[54] CATALYTIC PROCESS FOR PREPARING DIALKYL PHOSPHORODITHIOIC ACIDS

[75] Inventor: Stanley B. Mirviss, Stamford, Conn.

[73] Assignee: ICI Americas Inc., Wilmington, Del.

[21] Appl. No.: 162,989

[22] Filed: Mar. 16, 1988

Related U.S. Application Data

[63] Continuation-in-part of Ser. No. 32,116, Mar. 30, 1987, abandoned.

[51] Int. Cl.$^5$ ............................................. C07F 9/02
[52] U.S. Cl. .................................................... 558/112
[58] Field of Search .......................................... 558/112

*Primary Examiner*—Anton H. Sutto
*Attorney, Agent, or Firm*—Denis A. Polyn

[57] ABSTRACT

The formation of dialkyl phosphorodithioic acids by reacting phosphorus pentasulfide with an alcohol is catalyzed by using an organosulfur halide catalyst for the reaction. Representative classes of organosulfur halide catalysts include the sulfonium halides, the sulfoxonium halides, and polymeric sulfur halide materials.

10 Claims, No Drawings

CATALYTIC PROCESS FOR PREPARING DIALKYL PHOSPHORODITHIOIC ACIDS

CROSS-REFERENCE TO RELATED APPLICATIONS

This application is a continuation-in-part of application Ser. No. 032,116, filed Mar. 30, 1987, now abandoned.

BACKGROUND OF THE PRESENT INVENTION

The present invention is a catalytic process for the manufacture of dialkyl phosphorodithoic acids by reacting phosphorus pentasulfide with an alcohol.

DESCRIPTION OF THE PRIOR ART

The process whereby dialkyl phosphorodithioic acids are manufactured by the reaction of phosphorus pentasulfide with an alcohol to form the desired dialkyl phosphorodithioic acid is well known. Moreover, a number of investigators have improved the basic reaction by proposing various types of compounds as catalysts for the reaction. For example, U.S. Pat. No. 4,083,899 proposes the use of a variety of compounds that all contain a nitrogen atom therein to promote the reaction. More recently, U.S. Pat. No. 4,397,791 proposed the use of various phosphorus compounds (phosphonium salts, phosphine oxides, phosphine sulfides and phosphinic acid derivatives) as well as ammonium salts as catalysts for the reaction of phosphorus pentasulfide and an alcohol. The basic theme of either using nitrogen or phosphorus-based catalysts is echoed by Japanese Kokai Nos. 58/32889 and 58/32888 as well.

The present invention relates to the use of a novel class of catalysts for the reaction of phosphorus pentasulfide and an alcohol to form a dialkyl phosphorodithioic acid.

SUMMARY OF THE PRESENT INVENTION

The present invention relies upon the use of a catalytically effective amount of an organosulfur halide catalyst for the promotion of the reaction between phosphorus pentasulfide and an alcohol to form the desired dialkyl phosphorodithioic acid. Representative classes of organosulfur halide catalysts include sulfonium halides, sulfoxonium halides, and polymeric sulfur halides.

DETAILED DESCRIPTION OF THE PRESENT INVENTION

The basic outlines of the present invention follow the known technology whereby a lower alkyl alcohol, e.g. one containing an alkyl group of from about 1 to about 12 carbon atoms, an aryl alcohol such as phenol, an alkylaryl alcohol, or arylalkyl alcohol, a substituted aryl alcohol, a substituted alkylaryl alcohol or an arylalkyl alcohol wherein the alkyl group contains from 1 to about 12 carbon atoms and the substitutions are halogen, preferably iodine, chlorine and bromine, $C_1$-$C_4$ alkyl or $C_1$-$C_4$ alkoxy groups, is reacted with phosphorus pentasulfide at temperatures ranging from about 30° C. to about 125° C. in order to form a dialkyl phosphorodithioic acid.

In accordance with the present invention, the above general type of process is catalytically enhanced by the presence of a catalytically effective amount (from about 0.01% by weight to about 3.0% by weight, more preferably 0.01% by weight to about 3.0% by weight and most preferably 0.05% by weight to about 1.0% by weight of the reactants) of an organosulfur halide catalyst which is effective to achieve the desired level of promotion.

One representative class of compounds which can be used as the organosulfur halide catalyst in accordance with the present invention is the sulfonium halides. These compounds are represented by the general formula $(R)_3SX$, where R can be an alkyl group, an aryl group, an alkylaryl group or an arylalkyl group, and X is halogen. Preferred halogens for use are iodine, chlorine and bromine. If desired, the substituents R that are contained in the sulfonium halide catalyst can either be unsubstituted or can be substituted with non-interfering substituents for the catalytic reaction desired herein. Generally speaking, the alkyl groups can range anywhere from about 1 to about 12 carbon atoms. The aryl groups may range from 6 to 10 or more carbon atoms.

Another class of organosulfur halide catalysts in accordance with the present invention are the sulfoxonium halide salts represented by the formula $(R)_3S(O)X$, where R and X are defined as above.

Another representative class of organosulfur halide catalysts for use in the present invention include polymeric sulfur halides having a cation of the general formula $-[C-C-S(R)-C-]^+_n$ which is associated with a halide anion such as fluorine, chlorine, bromine or iodine. Preferably, an iodide, chloride or bromide ion is present. These polymeric sulfur halides can be formed by the polymerization of thiiranes (episulfides) followed by quaternization with an alkyl halide.

The present invention is further illustrated by the examples which follow.

EXAMPLE 1

This is a control run and does not illustrate the present invention.

A 500 milliliter (ml) round-bottom, three-neck flask was fitted with a stirrer, condenser, thermometer, dropping funnel and cooling bath. A caustic scrubber was connected to the condenser and to a gentle nitrogen gaseous sweep. The flask was charged with 111 grams (g) (0.5 mol) of 20 mesh phosphorus pentasulfide. Then 94 g of ethanol containing 0.5 volume % benzene (2.0 mol) was added with stirring from the dropping funnel maintaining the temperatures at 50°–60° C., as needed, with cooling. The reaction mixture was stirred for an additional hour at 50°–60° C. After cooling, the reaction mixture was filtrated to remove unreacted phosphorus pentasulfide. The filtrate was held for one hour under vacuum at 40°–50° C. and had a final weight of 182 g (98% yield). Analysis by gas chromatography showed a product purity of 75.9%.

EXAMPLE 2

This run used the same procedure as employed in Example 1 except that 0.6 g of trimethylsulfonium iodide was added to the phosphorus pentasulfide before the addition of the ethanol. The filtrate had a weight of 182.5 g (98% yield), and gas chromatographic analysis showed a product purity of 82.6% (i.e., 6.7% higher than the control run of Example 1).

EXAMPLE 3

This is another control run and does not illustrate the present invention.

The procedure used was similar to that of Example 1 with the exception that a different sample of phosphorus pentasulfide was used. The filtrate had a weight of 100.5 g (97% yield) and gas chromatographic analysis showed a product purity of 80.2%.

EXAMPLE 4

The procedure of Example 3 was used with the exception that 0.7% of trimethylsulfonium iodide was added to the phosphorus pentasulfide before the addition of the ethanol. The filtrate had a weight of 100.5 g (97% yield) and a product purity of 86.1% was achieved as measured by gas chromatography. This was 5.9% higher than the control run (Example 3).

EXAMPLES 5-9

Five control runs for Examples 10-21 were made. They do not illustrate the present invention.

A 500 ml, round-bottom, three-necked flask fitted as in Example 1 was charged with 58.3 g of phosphorus pentasulfide (0.263 mol). Then 46.0 g of ethanol (1.0 mol) was added dropwise over a period of 15 min. at 50°–55° C. The reaction was stirred for 10 min. at 50°–55° C. Then 58.3 g (0.263 mol) of phosphorus pentasulfide was added, followed by 46.0 g of ethanol added over a period of 30 min. at 50°–55° C. The reaction was stirred an additional 30 min. at 50°–55° C. The reaction mixture was filtered to remove any unreacted phosphorus pentasulfide. The filtrate was held under vacuum for 30 min. while warm to remove hydrogen sulfide and unreacted alcohol. The products were analyzed by NaOH titration and gas chromatograph for purity and yield and the average results are presented in Table 1.

EXAMPLES 10-21

The same procedure as used in Examples 5-9 above was used except that a predetermined amount of catalyst was dissolved in the first 46 g ethanol addition.

The results of Examples 5-21 are presented in Table 1.

TABLE 1

| Example | Catalyst Weight % and Catalyst | Wt. Purity By NaOH Titration | Wt. Purity By GC Analysis | Mole & Yield Corr. for Purity NaOH Titration | Mole & Yield Corr. for Purity GC Analysis |
|---|---|---|---|---|---|
| 5-9 | None | 89.5 (average) | 78.2 (average) | 82.0 (average) | 69.8 (average) |
| 10 | 0.2(CH$_3$)$_3$SI | 95.6 | 81.2 | 91.1 | 77.4 |
| 11 | 0.2(CH$_3$)$_3$SBr | 94.0 | 82.3 | 88.9 | 77.9 |
| 12 | 0.1(CH$_3$)$_3$SBr | 93.0 | 84.9 | 86.2 | 78.7 |
| 13 | 0.05(CH$_3$)$_3$SBr | 89.1 | — | 83.3 | — |
| 14 | 0.2(C$_2$H$_5$)$_3$SBF$_4$ | 92.1 | 82.5 | 87.9 | 78.7 |
| 15 | 0.6(C$_6$H$_5$)$_3$SCl | 97.3 | 85.3 | 94.4 | 84.9 |
| 16 | 0.4(C$_6$H$_5$)$_3$SCl | 96.0 | 85.0 | 93.6 | 82.9 |
| 17 | 0.2(C$_6$H$_5$)$_3$SCl | 95.9 | 86.9 | 91.3 | 84.7 |
| 18 | 0.1(C$_6$H$_5$)$_3$SCl | 94.2 | 84.6 | 90.6 | 81.4 |
| 19 | 0.05(C$_6$H$_5$)$_3$SCl | 91.8 | 85.6 | 86.9 | 81.0 |
| 20 | 0.2(CH$_3$)$_3$SOI | 89.3 | — | 82.9 | — |
| 21 | 0.2(CH$_3$)$_3$SOCl | 92.1 | 80.1 | 86.2 | 75.0 |

CG = Gas chromatograph.

EXAMPLE 22

This is a control run for Examples 23 and 24 and does not illustrate the present invention.

A sample of phosphorus pentasulfide was heated at 280° C. for 24 hours to decrease the reactivity (by increasing the crystallinity and decreasing the P$_4$S$_9$ content).

A 250 ml, round-bottom, three-necked flask was charged with 38.8 g (0.175 mol) of the above treated phosphorus pentasulfide. Then 30.6 g of ethanol (0.665 mol) was added at 50°–55° C. over a period of 30 min. with good stirring. The reaction was stirred an additional 15 min. at 55° C. Another 30.6 g of ethanol was added at 55° C. over a period of 30 min., followed by an additional 30 min. of stirring at 60° C. The reaction mixture was filtered to remove unreacted phosphorus pentasulfide (10.5 g but 6.7 g subtracting the excess, 3.8 g, of phosphorus pentasulfide used). The assay by sodium hydroxide titration was 86.2% but 83.2% by gas chromatotography. The mole % yield corrected for NaOH assay was 77.3% and corrected for GC analysis was 75%. A repeat run gave: (1) 6.5 g of unreacted phosphorus pentasulfide (after subtraction of the excess used): (2) an NaOH assay of 84.8%; (3) a GC purity of 82.3%; and (4) corrected mole % yields of 77.1% (NaOH assay) and 75% (GC analysis).

EXAMPLES 23 AND 24

The same procedure as in Example 22 above was used except that a predetermined amount of triphenyl sulfonium chloride was also used in the initial charge to the reaction.

The results of Examples 22-24 are presented in Table 2.

TABLE 2

| Example | Catalyst Weight % and Catalyst | g P$_2$S$_5$ Left[a] | Wt. Purity By NaOH Titration | Wt. Purity By GC Anal. | Mole % Yield Corr. for Purity NaOH Titration | Mole % Yield Corr. for Purity GC Anal. |
|---|---|---|---|---|---|---|
| 22[b] | None | 6.6 | 85.5 | 82.8 | 77.2 | 75 |
| 23 | 0.2(C$_6$H$_5$)$_3$SCl | 0 | 88.9 | — | 81.8 | — |
| 24 | 0.6(C$_6$H$_5$)$_3$SCl | 0 | 89.2 | 91.4 | 8.1 | 84 |

[a]After subtracting excess used.
[b]Average of two runs.

The improvement in product purity was even greater than that attainable from the original phosphorus pentasulfide before annealing, which gave 87.8% by NaOH titration (average of 3 runs) and 79.3% by GC analysis. The mole % corrected yield (by NaOH titration) was equivalent, 82.4% (average of 3) but much less by GC analysis, 74.2% (average of 3). All of the phosphorus pentasulfide (equivalent to the alcohol added) reacts when catalyst is used.

EXAMPLE 25

This is a control run for Example 26 and does not illustrate the present invention.

A 250 ml flask was charged with 36.4 g of phosphorus pentasulfide (0.164 mol) (5% excess) and 20 g of methanol (0.625 mol) was added over 30 min. at 45°–50° C. The reaction was stirred an additional 30 min. at 50° C. Another 36.4 g of phosphorus pentasulfide was added, followed by 20.0 g of methanol added in 30 min. at 50° C. The reaction was stirred an additional 30 min. at 55° C. The product was analyzed by NaOH titration and gas chromatography for purity and yield.

EXAMPLE 26

The reaction above was repeated except that 0.146 g of triphenylsulfonium chloride (0.2 wt. % on $P_2S_5$) was added with the initial charge of phosphorus pentasulfide.

The results of Examples 25 and 26 are presented in Table 3.

TABLE 3

| Example | Catalyst Wt. % and Catalyst | NaOH Titration Assay | Mole % Yield Corrected for Assay |
|---|---|---|---|
| 25 | None | 84.5 | 72.8 |
| 26 | 0.2 | 92.0 | 82.3 |

EXAMPLES 27–30

The experimetns were carried out as in Examples 25 and 26 using a different $P_2S_5$. Example 27 is a control run. The results are presented in Table 4.

TABLE 4

| Example | Catalyst Wt. % and Catalyst | % Purity by NaOH Titration | GC Analysis | Mole % Yield Corrected For Assay |
|---|---|---|---|---|
| 27[a] | None | 84.3 | 83.2 | 76.6 |
| 28 | 0.1($C_6H_5)_3SCl$ | 87.9 | 85.7 | 81.2 |
| 29 | 0.1($C_6H_5)_3SCl$ | 89.0 | 87.7 | 82.2 |
| 30 | 0.2($C_6H_5)_3SCl$ | 92.2 | 91.0 | 88.1 |

[a]Average of two runs.

EXAMPLE 31

This is a control run for Examples 32–35 and does not show the present invention.

A 500 ml flask was charged with 41.6 g (0.185 mol) of phosphorus pentasulfide and then was added 58.4 g of a mixture of n-amyl, isoamyl and isobutyl alcohols (0.74 mol) over 15 min. at 80° C. The reaction was stirred an additional 15 min. at 80° C. Then 41.6 g of $PS_5$ was added, followed by 58.4 g of the $C_4$-$C_5$ alcohol mix. The reaction mixture was then stirred an additional 2 hours at 80° C. The reaction mixture was then filtered to remove unreacted $P_2S_5$. The product was analyzed by NaOH titration and gas chromatography for purity and yield.

EXAMPLES 32–35

These runs were made as for the control run except that the triphenylsulfonium chloride catalyst was added with the initial charge of $P_2S_5$. The results are presented in Table 5.

TABLE 5

| Example | Catalyst Wt. % and Catalyst | Wt. Product g | Wt. % Purity by GC |
|---|---|---|---|
| 31[a] | None | 181.9 | 90.8 |
| 32 | 0.2($C_6H_5)_3SCl$ | 180.2 | 95.3 |
| 33 | 0.4($C_6H_5)_3SCl$ | 181.3 | 98.5 |
| 34 | 0.6($C_6H_5)_3SCl$ | 183.4 | 98.0 |
| 35 | 0.6($C_6H_5)_3SCl$ | 181.0 | 97.2 |

[a]Average of four runs.

EXAMPLE 36

A Dewar flask fitted with a thermometer and stirrer was charged with 300 ml of ethanol and the temperature recorded. Then 20.0 g of phosphorus pentasulfide was added quickly with stirring and the temperature was recorded periodically until the temperature no longer rose. During the first 60–85% of the reaction, the rate of temperature increase was linear with time. The slope of the linear portion of the temperature vs. time plot was calculated. The results are tabulated below with and without catalysts added with the ethanol.

| Wt. % Cat. on $P_2S_5$ | % Increase in Slope Over Control |
|---|---|
| None (control) | — |
| 0.2($C_6H_5)_3SCl$ | 34 |
| 0.6($C_6H_5)_3SCl$ | 104 |
| 0.2($CH_3)_3SI$ | 16 |
| 0.2($CH_3)_3SBr$ | 13 |
| 0.2($C_2H_5)_3SBF_4$ | 40 |

EXAMPLE 37

This is a control run for Example 38 and does not illustrate the present invention.

A 500 ml round-bottom flask fitted as in previous examples was charged with 186 g of phenol (1.98 mol). The phenol was heated to 80° C. with stirring and then was added 111 g of phosphorus pentasulfide (0.50 mol) slowly with stirring over a period of 10 min. There were no obvious signs of reaction. The reaction was stirred for 2 hrs. at 90°–102° C. without any significant reaction. The temperature was raised to about 115° C. when apparent reaction started. The temperature was kept at about 115° C. for 1 hr. Most, but not all, of the $P_2S_5$ had reacted. Filtration gave 24 g of unreacted $P_2S_5$.

EXAMPLE 38

The same equipment and reagents were used as above except that 0.22 g of triphenylsulfonium chloride (0.2 wt. % on $P_2S_5$) was added to the phenol prior to the $P_2S_5$ addition. There was no apparent reaction of the $P_2S_5$ and phenol at 80° C. The temperature was raised to 90°–95° C. and vigorous reaction started as noted by $H_2S$ evolution and the appearance of a dark brown color. After 60 min. more of stirring at 90°–95° C., all of the $P_2S_5$ had reacted as noted by subsequent filtration of the reaction product. Thus, the reacton starts at a lower temperature (20°–25° C. lower) than without catalyst and goes to completion, which is not the case without catalyst.

The foregoing examples are merely presented to illustrate certain preferred embodiments of the present invention and should not be construed in a limiting sense. The scope of protection that is sought is set forth in the claims which follow.

What is claimed is:

1. A process for catalyzing the reaction of phosphorus pentasulfide with an alkyl alcohol, aryl alcohol, alklaryl alcohol, arylalkyl alcohol, substituted aryl alcohol, substituted alkylaryl alcohol or substituted arylalkyl alcohol to form a dialkyl or diaryl phosphorodithioic acid which comprises using a catalytically effective amount of a sulfonium halide or sulfoxonium halide salt catalyst for the reaction.

2. A process as claimed in claim 1 wherein a sulfonium halide catalyst is used.

3. A process as claimed in claim 1 wherein a sulfoxonium halide catalyst is used.

4. A process as claimed in claim 2 wherein the sulfonium halide contains $C_1$-$C_{12}$ alkyl groups.

5. A process as claimed in claim 3 wherein the sulfoxonium halide contains $C_1$-$C_{12}$ alkyl groups.

6. A process as claimed in claim 2 wherein the sulfonium halide contains $C_6$-$C_{10}$ aryl groups.

7. A process as claimed in any of claims 2-3 wherein the halide is an iodide.

8. A process as claimed in any of claims 2-3 wherein the halide is a chloride.

9. A process as claimed in any of claims 2-3 wherein the halide is a bromide.

10. A process as claimed in any of claims 2-3 wherein the amount of catalyst ranges from about 0.01% to about 3.0% by weight of the reactants.

* * * * *